United States Patent [19]

Sturtevant et al.

[11] 4,148,836
[45] Apr. 10, 1979

[54] PROCESS FOR REDUCING WATER CONTENT OF SULFURIC ACID IN HYDROCARBON ALKYLATIONS

[75] Inventors: Robert L. Sturtevant, Baldwinsville; Bela I. Karsay, DeWitt; Alan B. Gancy, Syracuse, all of N.Y.

[73] Assignee: Allied Chemical Corporation, Morris Township, N.J.

[21] Appl. No.: 863,656

[22] Filed: Dec. 23, 1977

[51] Int. Cl.² ............................................ C07C 3/54
[52] U.S. Cl. ........................................... 260/683.62
[58] Field of Search ............... 260/683.59, 683.62, 260/671 R, 683.63; 423/531, 525, 522

[56] References Cited

U.S. PATENT DOCUMENTS

| | | | |
|---|---|---|---|
| 2,071,598 | 2/1937 | Girsewald et al. | 423/522 |
| 2,435,402 | 2/1948 | McAllister et al. | 260/683.63 |
| 2,593,128 | 4/1952 | Felter | 423/525 |
| 2,863,724 | 12/1958 | Skelly et al. | 260/683.62 |

*Primary Examiner*—George Crasanakis
*Attorney, Agent, or Firm*—Anthony J. Stewart; Thomas D. Hoffman

[57] ABSTRACT

An improved process for the alkylation of isoparaffins by olefins in the presence of a sulfuric acid catalyst is disclosed. Improvement in the octane rating of the product alkylate is achieved by the periodic fortification of the sulfuric acid catalyst with sulfur trioxide-bearing fortifying agents and the incorporation of a holding time to delay the return of the fortified acid to the alkylation zone. Fortification is employed less than 6% of the time the catalyst is in contact with the hydrocarbons and a preferred water content of between 1.5% and 2.5% is maintained in the acid. By maintaining an optimum water content and fortifying less frequently, lower water and organic build-up rates are observed than previously thought possible. By incorporation of a holding time before the acid is returned to the alkylation reactor, there is essentially complete utilization of the fortifying agent for water removal and no free $SO_3$ is available for harmful side reactions with the hydrocarbon feeds in the reactor. When the organic impurities dispersed in the recycle acid are more completely removed prior to periodic fortification, a wider range of $SO_3$-bearing agents can be applied than previously thought possible. This nondestructive, periodic fortification process effects improvement in the octane rating of the product alkylate while simultaneously extending the service life of the sulfuric acid catalyst by allowing use of the acid to a higher final organic content.

5 Claims, 1 Drawing Figure

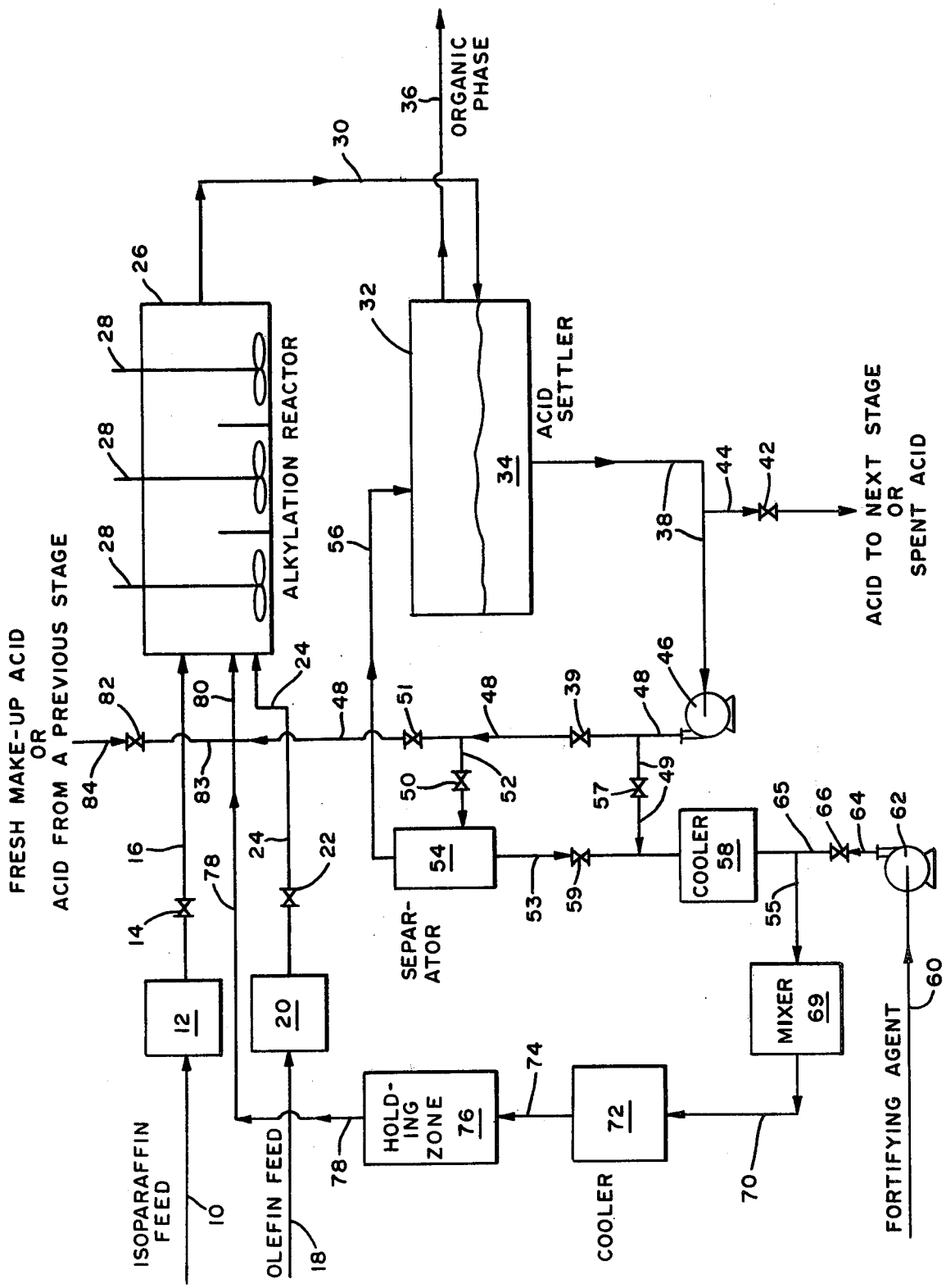

PROCESS FOR REDUCING WATER CONTENT OF SULFURIC ACID IN HYDROCARBON ALKYLATIONS

II. BACKGROUND OF THE INVENTION

1. Field of the Invention

This invention relates to an improved alkylation process for the production of premium grade (high octane number) gasoline by the petroleum industry. More particularly, this invention relates to an improved alkylation process which increases the octane rating of the product alkylate and simultaneously prolongs the catalytic effectiveness of the sulfuric acid by periodic fortification of the alkylation acid and incorporation of a holding time to delay the return of the fortified acid to the alkylation zone.

2. Description of the Prior Art

It is common practice in petroleum refineries to treat low boiling isoparaffins or alkanes with alkylating reagents such as olefins, in the presence of a sulfuric acid catalyst to produce a high octane alkylate, boiling in the gasoline range. It is well known that the sulfuric acid catalyst does not undergo major chemical change during the alkylation process but the acid concentration diminishes due to the build-up of water and organic impurities or red oils originating from undesired side reactions. As the build-up of these diluents approaches 10–12%, the concentration of the alkylation acid is reduced from its original value of about 98.0–99.5% to about 88–90%. At these lower concentration values, the catalytic activity of the alkylation acid is decreased and the octane number of the product alkylate is undesirably lower. At this point the alkylation acid must be withdrawn from the system and reprocessed by regeneration. In reprocessing, the spent acid is usually thermally decomposed to sulfur dioxide, carbon dioxide and water. After purification, the sulfur dioxide generated is reconverted to sulfuric acid by the conventional contact process.

Besides the fuel and energy required for the acid regeneration, another obvious disadvantage of this widely used destructive regeneration process is that the spent acid, consisting mostly (88–90%), of sulfuric acid, is completely decomposed to eliminate the relatively small amounts of water (3–5% by weight) and organic impurities (3–8% by weight). Analyses of spent or used alkylation acid vary somewhat depending on the operating conditions.

In an attempt to overcome these difficulties and extend the effective service life of the alkylation acid, numerous investigations have been directed to understanding the operating variables of the alkylation process which affect the alkylate quality. The importance of a high acid concentration and the maintenance of a constant water content in the alkylation acid is disclosed by U.S. Pat. No. 2,242,845. In the specifications of this U.S. patent, it has been proposed that more concentrated sulfuric acid, for example 98–103% $H_2SO_4$, be used as the make-up acid to maintain the strength of the alkylation acid between a concentration of about from 88.0% to 95% and preferably to 91% by weight $H_2SO_4$. Alternately, it is disclosed that partially spent acid may be withdrawn from the system and the above concentration range be maintained by fortification with $SO_3$ or fuming sulfuric acid.

U.S. Pat. No. 2,437,091 discloses that free $SO_3$, which rapidly attacks the hydrocarbons in the alkylation acid, and water, which is built-up in the system by side reactions during the alkylation, are deleterious both to the alkylate quality as measured by the octane number (O.N.) and the effective service life time of alkylation acid. This patent, U.S. Pat. No. 2,437,091, teaches that part of the alkylation acid be continuously discharged and the balance prechilled and thence continuously fortified with fuming $H_2SO_4$ or $SO_3$ to maintain a water content in the system below 4% by weight and preferably below 1% by weight.

In U.S. Pat. No. 2,465,049, $SO_3$ or fuming $H_2SO_4$ is continuously applied to the alkylation acid and the hydrocarbon feedstocks in a mixer immediately before the alkylation zone to dehydrate the feeds and to convert the water content therein to additional $H_2SO_4$ catalyst. A slight excess of a $SO_3$-bearing fortifying agent, over that required to react with the water in the hydrocarbon feeds, is applied to remove the water generated by side reactions within the alkylation zone.

In spite of these investigations of the alkylation process, it is still recognized by the petroleum industry that a practical fortification process is needed.

It is an object of the present invention to provide a process for maximizing the octane rating of alkylate product and thereby effectively improving the alkylate yield.

It is another object of this invention to provide a process for reducing the rates of water and organic impurities built-up in the alkylation acid.

It is a further object of this invention to provide a process for fortifying the alkylation catalyst with $SO_3$-bearing agents under conditions which minimize the exposure of the fortifying agents to the organic matter dissolved in the acid catalyst.

Still another object of this invention is the extension of the effective service life time of the acid catalyst and the reduction in the quantity of spent acid subject to destructive regeneration.

III. SUMMARY OF THE INVENTION

In satisfaction of the objects and advantages, detailed above, there is provided by this invention an improved process for the periodic fortification of the sulfuric acid catalyst for the alkylation of hydrocarbons which comprises an alkylation zone wherein in alkylatable $C_4$–$C_5$ isoparaffin feed stocks are contacted with alkylating agents ($C_2$–$C_5$ olefins) in the presence of a concentrated sulfuric acid catalyst containing at least about 1.0% but less than 4% by weight water, under alkylation conditions in an alkylation reactor equipped with agitators, and wherein the organic phase is separated from the acid catalyst phase, the acid catalyst is cooled and recycled to the alkylation reactor, and wherein the water content of the alkylation acid is maintained by addition thereto of sulfur trioxide fortifying agents. The improvement comprises: (1) prior to the addition of the sulfur trioxide, removing the organic impurities dispersed in the acid catalyst; (2) periodically introducing the sulfur trioxide into the acid catalyst, the periodic introduction being for a time less than 6% of the time (as hereinafter defined) the acid catalyst is in contact with the hydrocarbons; (3) thereafter cooling the fortified acid catalyst to remove the heat generated by the periodic introduction of the sulfur trioxide; and (4) delaying the return of the fortified acid catalyst to the alkylation reactor for a time sufficient to allow substantially all of the sulfur trioxide to react with water present in the alkylation acid. The alkylation acid is fortified less frequently and the water content of the acid catalyst is allowed to vary within the optimum range of more than about 1.0% and less than about 4.0% by weight.

In accordance with the present invention, it has been found, surprisingly, that by more complete removal of the hydrocarbons in the alkylation catalyst and by incorporation of a holding time into the periodic fortification process, the octane rating of the alkylate is increased while simultaneously extending the service life time of the alkylation acid. To minimize the exposure of the $SO_3$ to the organic matter dissolved and dispersed in the alkylation acid, a more complete elimination of the removable organics is accomplished by settling and phase separation, as it is currently practiced, followed by passing the acid through a more efficient separator, such as a hydrocyclone, and optionally by depressurizing the acid. The dispersed or emulsified hydrocarbons and alkylate are removed in the acid settler (and in the more efficient separator), while dissolved volatile hydrocarbons are removed by depressurization. To maximize the utilization of the $SO_3$ for reaction with the water content of the alkylation acid, a holding time is incorporated into the periodic fortification process. This holding time is provided after periodic fortification and before the fortified acid is returned to the alkylator. It has been found that in the absence of a holding time, the fortification reaction, which is relatively slow, cannot go to completion, and the fortified acid, when recycled to the alkylation zone, still contains highly reactive ingredients of the fortifying agent. These reactive species, instead of interacting with the relatively low (0.5–4%) water content of the acid, can more easily attack the hydrocarbon feeds present in higher concentration in the alkylation zone and can convert the feeds to acid soluble, stble compounds and water. It has been found, unexpectedly, that maintenance of a constant water content in the alkylation acid below about 1.5% by weight by a typical continuous fortification process of the prior art, accelerates the build-up of water, organic impurities and red oils in the acid and thereby produces a shorter service life time for the sulfuric acid than when the water content is allowed to vary and the acid catalyst is fortified periodically in accordance with this invention. Allowing the water content of the alkylation acid to vary within the optimum range of above about 1.0% and below about 4.0%, preferably about 1.5 to about 2.5% and applying the $SO_3$-bearing fortifying agents periodically, in accordance with this invention, results in relatively low (0.8 to 1.7% per 100 cycles) build-up rates of water in the acid and consequently the buildup of organic impurities can be tolerated over a longer time. The significant extension of service life of the acid catalyst achieved by this invention is due to the fact that the catalytic activity of the alkylation acid at relatively low water content can be maintained even though the acid has a higher final organic content than previously thought possible.

When the periodic fortification of the alkylation acid is performed in accordance with this invention, the quantity of $SO_3$ needed to return the water content in the acid catalyst to its optimum value corresponds almost exactly to the theoretical amount required. When applied in accordance with this invention, the concentration has little effect on the build-up rates of water and organic impurities in the alkylation acid. This is governed by the concentration of the resulting fortified acid. For this reason, oleum of any strength, from the weakest to 65%, or even 100% liquid sulfur trioxide may be used, with practically identical results. Economic considerations may make 13–30% oleum the preferable fortifying agent.

The frequency of fortification depends upon the rate of water build-up in the acid. This build-up in turn, is a function of several variables, such as the type of hydrocarbons used in the alkylation, the moisture content of these hydrocarbons, the initial acid concentration and others detailed below. Low water build-up rates require less frequent fortification while high water build-up rates can be compensated for by more frequent fortification with larger quantities of fortifying agent.

For purposes of this invention, the term "cycle" represents the equivalent of one passage of the entire acid volume or inventory through an alkylation reactor while "cycle time" means the time needed to permit this volume of acid to flow through the system. When reference is made herein to percent of the time the acid catalyst is in contact with the hydrocarbons, it is to be understood that this is in reference to one hundred complete cycles. For example, fortifiction every second cycle would be 50% of the time the acid catalyst is in contact with the hydrocarbons and once every hundred cycles would be 1% of the time.

BRIEF DESCRIPTION OF THE DRAWINGS

The present invention is more clearly illustrated in the attached drawing. FIG. 1 is a schematic view of a single stage alkylation unit incorporating the principles of the present invention.

DETAILED DESCRIPTION OF THE INVENTION AND OF THE PREFERRED EMBODIMENTS

Referring to FIG. 1, liquified $C_4$–$C_5$ isoparaffin feed from line 10, after passing through a suitable drier 12 and valve 14 is introduced under pressure via line 16 into the alkylation reactor 26, equipped with agitators 28. Reactor 26 may be any conventional or suitable type of reactor. The liquified olefin feed which may be a mixture of $C_2$ to $C_5$ olefins from a refinery cracking unit (not shown), is passed under pressure by line 18 through a suitable drier 20 and valve 22 which regulates the flow through line 24 into the stirred alkylation reactor 26. Valves 14 and 22 are regulated to adjust the molar ratio of isoparaffin to olefin in the hydrocarbon feed to 4–10:1, preferably 4–7:1. The olefin and isoparaffin feeds supplied to reactor 26 may advantageously be caustic — washed and then water washed. While predrying of the hydrocarbon feeds is the preferred procedure, it is to be understood that this is not essential.

Fresh make-up acid or acid from a previous stage (not shown) is introduced from line 84 via valve 82 into line 83 and thence into reactor 26 via line 80. The acid catalyst is maintained temperature below 25° C. before introduction to reactor 26. Generally, the acid catalyst is contacted with the hydrocarbon feeds for an average period of time of at least 5 minutes and not more than 20 minutes. The alkylation mixture is stirred at a temperature between 10° and 20° C., preferably 10° C. This temperature may be maintained by the partial evaporation of the volatile hydrocarbon phase in reactor 26. Heat generated in the reactor 26 can be removed by suitable exchangers (not shown). The alkylation reaction mixture is discharged from reactor 26 by line 30 and introduced into acid settler 32. Herein separate organic and acid phases are formed, and the separated organic phase is removed by line 36 for passage to suitable equipment for caustic-washing and then water-washing and thence to fractionation towers (not shown). The isobutane recovered via fractionation can be recycled to line 10.

The acid layer 34 in settler 32 is continuously removed from settler 32 via line 38. A portion of the acid catalyst, which is approximately equivalent to the volume of make-up acid or acid added from a previous stage into line 83 via line 84 and valve 82, is continuously withdrawn from line 38 via line 44 and valve 42. The rest of the acid catalyst is recycled through pump 46 and line 48, a series of valves and thence through line 80 into reactor 26, until about 0.2–0.5% water has built-up over and above the optimum value. Then, the acid is taken out of the return line 48 via valve 57 and passes through line 49, valve 57 to line 55 which is introduced, by line 65 through valve 66, a predetermined amount of a $SO_3$-bearing fortifying agent. Any commercially available gaseous or liquified $SO_3$-bearing fortifying agent can be used if applied in accordance with the present invention. Various oleums (13% 16%, 20%, 30% and 65%), 100% liquid $SO_3$, and even converter gas are suitable. Liquid $SO_3$, containing stabilizers, is preferably treated to separate the stabilizers before use. For this reason oleum or nonstabilized $SO_3$-bearing fortifying agents are preferred. When an amount of fortifying agent necessary to reduce the water content to the desired concentration is periodically added to the recycled acid catalyst at a temperature between 20° and 25° C., during one cycle, and with good agitation, the return of the fortified acid is delayed for a period of time of at least 5 minutes and not more than 60 minutes. In contrast, the continuous, as opposed to periodic, addition of $SO_3$ fortifying agents can cause a rapid build-up of acid soluble, high molecular weight, organic matter and may lead to the formation of carbonaceous materials or tarlike products. These harmful effects are obviated when $SO_3$-bearing fortifying agents are applied in accordance with the present invention.

It is important to note that not all the water present in the acid is removed, nor is the water content maintained at a constant value. It has been discovered that the water and organic impurities build-up rates are not constant and that these rates increase as the water content of the acid diminishes. At a preferred water content of 1.5–2.5%, the rates reach relatively low values which remain practically constant up to a water content of about 4%. When the fortification is performed periodically according to the present invention, it is found that the amounts of $SO_3$-bearing fortifying agent needed to return the water content of the acid to this preferred range of 1.5–2.5%, is essentially equivalent to the calculated amount.

The fortified recycle acid is passed from the mixer 69 through line 70 to a cooler 72 wherein the temperature of the fortified acid is maintained at a temperture between 10° and 20° C. The fortified acid is passed from the cooler 72 through line 74 into holding zone 76 wherein the temperature of the fortified sulfuric acid catalyst is maintained between 20° and 25° C. for a period of time of at least 5 minutes and not more than 60 minutes, preferably not more than 30 before return of acid to reactor 26 via lines 78, and 80. Suitable heat exchangers (not shown), are required to remove the heat generated by the reaction of $SO_3$ with the water content of the recycled acid.

The holding zone 76 may be any suitable design and a volume sufficient to contain the quantity of fortified acid so delayed. The purpose of this holding step is to allow the fortification reaction, which is relatively slow, to go to completion in a region, outside of the reaction zone, wherein the organic content of the acid and the chance for harmful side reactions of the $SO_3$ with the organics dissolved in acid are the lowest.

The $SO_3$, added in the form of oleum is not free but probably present as pyrosulfuric acid, $H_2S_2O_7$, in the bulk sulfuric acid. The water content of the acid catalyst is extensively solvated by the bulk acid. Thus the desired reaction between the added $SO_3$ and water to form $H_2SO_4$ is not instantaneous but requires a finite period of time to reach completion. By incorporation of a holding time in the periodic fortification process prior to the return of the acid to the alkylation zone a larger reduction in the rates of build-up of water and organic impurities in the acid is achieved than previously thought possible. By allowing the water content to vary within selected limits and applying the $SO_3$ fortifying agents less frequently, preferably 2–4% of the time the acid catalyst is in contact with the hydrocarbons, exposure of reactive organics to the $SO_3$ is minimized and essentially 100% utilization of the $SO_3$ fortifying agent for water removal is achieved. Thus, application of fortifying agents in accordance with the present invention allows efficient use of the sulfuric acid alkylation catalyst to a higher final organic content while simultaneously increasing the octane rating of the alkylate. By extension of the service life of the acid, the quantity of make-up acid and the amount of spent acid decomposed is lowered.

The amount of $SO_3$ required to return the acid to the optimum water content of between 1.0 and 4.0%, generally 1.2 to 2.5% is conveniently determined by monitoring the circulating acid. It is understood that line 60 will be equipped with a suitable flow meter, so that the desired amount of $SO_3$ required to react with the water content of the acid catalyst can be easily ascertained from the velocity of flow of the $SO_3$ — bearing fortifying agent and the $SO_3$ concentration therein as well as the amount of water in the acid catalyst.

The following Examples further illustrate the present invention and set forth the best mode presently contemplated for its practice.

EXAMPLES 1–6

Examples 1–6 illustrate alkylation using butene-1 as the olefin feed and isobutane or isopentane as the isoparaffin feed. This is not to be considered limiting since similar results are obtained with other olefins encountered in commercial alkylation processes, such as ethylene, propylene, butene-2, isobutylene and amylenes. Fresh (make-up) sulfuric acid, 99.0 to 99.5, generally 99.0 ash-free, is charged into an alkylation reactor similar to the one described in FIG. I, above. A stream of dried liquefied isobutane or isopentane and olefin in the molar ratio of 4:1 to 10:1, generally 10:1, is introduced into the reactor until the sulfuric acid to hydrocarbon volume ratio is about 60:40 to 55.45. It is well known that the sulfuric acid must be in excess to operate as an effective alkylation catalyst. The liquid hydrocarbons, and the acid are mixed by a high speed agitator in the reactor to disperse the hydrocarbons in the acid, and to allow the alkylation reaction to take place. Alkylations are generally conducted at temperatures between 10° and 20° C. and under pressure (40-80 psi) so that the hydrocarbons which are gases under ambient conditions are in liquid form in the alkylation reactor. The heat generated by the alkylation reaction can be removed by suitable heat exchangers (not shown).

When the sulfuric acid is periodically fortified, it is removed from line 48 via line 49, valve 57 and then cooled. An amount of 0.1-65% oleum, or liquid $SO_3$, is applied under somewhat higher pressure than the rest of the system via line 60, pump 62, line 64 and regulating valve 66 to the acid stream passing through line 55.

In a preferred embodiment of this invention, a more complete elimination of the organic impurities dispersed in the recycled acid is accomplished prior to the periodic application of the $SO_3$-fortifying agent by passing the sulfuric acid through an efficient separator 54, such as a hydrocyclone, and optionally by depressurizing the acid (not shown). Separated isobutane and alkylate are returned to the settler 32 via line 56. The purified acid catalyst is passed into cooler 58 via line 53 through valve 59. By more completely removing the organic impurities in the acid catalyst prior to the periodic application of the fortifying agent, essentially 100% utilization of the $SO_3$ for water removal is achieved. Since the water build up rate is lower when the water content of the acid is allowed to vary within the optimum range of 1.0 to 4% preferably 1.5 to 2.5%, the frequency of the application of the $SO_3$-bearing fortifying agent is lower. Since the dispersed organic impurities are more completely removed by the present invention, the harmful side reactions of $SO_3$ with the hydrocarbons in the acid catalyst are minimized and essentially all of the $SO_3$ is utilized for water removal.

Further, a wider choice of fortifying agents is available than previously thought possible. Even the more reactive and more commercially attractive converter gas ($SO_3$) can be applied in accordance with the present invention, with similar results, if the dispersed hydrocarbons are more efficiently separated and, optionally, the acid is depressurized prior to fortification thereof. It is also found that in this preferred embodiment of the present invention, a lower optimum water content of about 1.2% can be maintained in the acid, without higher build-up rates for water and organics. The maintenance of a lower water content permits the use of the sulfuric acid as an effective catalyst to a higher final organic content while simultaneously producing alkylate of higher octane rating than previously taught.

Results of Examples 1-6 are given in Table II, below.

EXAMPLE 1

This is a simulation of a single stage alkylation process without fortification and wherein both the water and organic content of the acid are allowed to build-up unimpeded.

Initial acid charge is 3,500g (1,900 mls) of 99.8% sulfuric acid, which is passed (cycled) 450 times through the alkylation reactor. The hydrocrbon feed is a 10:1 molar mixture of isobutane and butene-1. Feeding rate of acid is 36 cc/min, while that of the hydrocarbon mixture 24 cc/min. Average retention time in the reactor, which has a volume of 300 cc, is 5 minutes.

Acid samples are taken at frequent intervals: initially after every 5 cycles, later after every 25-50 cycles. The samples are analyzed for total acidity, free $H_2SO_4$, water and carbon contents. The difference between total acidity and free $H_2SO_4$ represents the percent of alkyl acid sulfates and aryl sulfonates present. Alkylate samples are taken about the same time as the acid samples, and are analyzed by a gas chromatograph for compositions. The octane number (O.N.) is calculated, in the standard way, from the composition.

Results of the analyses are summarized in Table I, below. From the % $H_2O$ and % C values in Table I, the build-up rates of water and organic impurities in various periods of the alkylation run are calculated, and the results per 100 cycles are listed in Table II, below. These build-up rates, as discussed above, are considered normal in a conventional alkylation.

Table I

Build-up of Water and Organic Impurities in Alkylation Acid in a Conventional Alkylation Process (Using No Fortification)

| Cycles Completed | % Titratable Acidity | % Free $H_2SO_4$ | % $H_2O$ | % C | O.N. of Alkylate |
|---|---|---|---|---|---|
| 0 | 99.8 | 99.8 | 0.2 | 0.0 | — |
| 20 | 96.4 | 95.3 | 0.9 | 1.2 | 94.2 |
| 25 | 96.5 | 95.5 | 0.8 | 1.4 | 94.4 |
| 50 | 95.7 | 94.8 | 1.3 | 1.8 | 94.6 |
| 100 | — | — | 1.7 | 2.5 | 95.0 |
| 150 | — | — | 2.1 | 3.5 | 95.1 |
| 200 | — | — | 2.4 | 3.9 | 94.6 |
| 400 | — | — | 3.4 | 6.0 | 92.0 |
| 450 | 89.3 | — | 4.0 | 6.7 | 91.4 |

EXAMPLE 2

This is a demonstration of a single stage fortification process of the prior art, wherein the alkylation acid is continuously fortified, cooled and forwarded to the alkylation reactor.

Initial acid charge is 1860g (1016 cc) of 98.0% $H_2SO_4$. all other conditions are the same as in Example 1. The acid is cycled 300 times through the alkylation reactor. During the passages of the acid through the system, a continuous stream of 65% oleum is added, with good agitation and cooling in a quantity to maintain the water content in the acid at 2%. Acid samples are withdrawn and analyzed on a regular basis. The build-up rates per 100 cycles of water and organics in the acid are 3.0% and 2.8%. respectively.

Table II

Effect of Method and Frequency of Fortification on the Build-up Rates of Water and Organic Impurities in the Alkylation Acid

| Example | Frequency of Fortification[+] | Build-up Rates per 100 passages of acid | | O.N. of Alkylate after 200 Cycles | O.N. of Alkylate after 400 cycles |
|---|---|---|---|---|---|
| | | Water | Org. Impurities | | |
| 1 | none | .84 | 1.5 | 94.6 | 92.0 |
| 2 | continuous (no holding) | 3.0 | 2.8 | 94.2 | —* |
| 3 | 20% (with holding) | 3.0 | 3.0 | 93.6 | —** |
| 4 | 6% (with holding) | 0.8 | 2.0 | 95.4 | 92.8 |
| 5 | 1-2% (with holding)[a] | 0.5 | 1.35 | 94.9 | 94.4 |
| 6 | 3-4% (with holding)[a] | 1.7 | 2.0 | 95.1 | 94.5 |

[+]Expressed as percent of the time the acid catalyst is in contact with the hydrocarbons.
[a]Includes passage of acid through an efficient separator prior to periodic fortification.
*The O.N. of alkylate is less than 91 after 300 cycles and thus the alkylation acid is discarded.
**The O.N. of alkylate is less than 91 after 250 cycles and thus the alkylation acid is discarded.

A comparison of the results of the first two examples (see Table II) shows that the rate of water build-up in a continuous fortification process is about 3.5 times higher than in an alkylation wherein the no fortification is employed. The corresponding carbon build-up rate is about twice as high as wherein the acid is not fortified.

EXAMPLE 3

This experiment is similar to Example 2 except for the method and frequency of application of the fortifying agent. The alkylation acid is passed through the system 250 times (cycles). After every 5 cycles, the sulfuric acid is withdrawn from the system and a quantity of 65% oleum is added, with good mixing, to return the acid to its original 2% water content. After fortification the return of the acid to the alkylation reactor is delayed for a period of time of 5 to 30 minutes. The rates of build-up of water and organics in the acid (see Table II, above) approach those observed in the Example 2 wherein continuous fortification is employed.

EXAMPLE 4

This experiment is similar to Exmple 3 except that the acid was passed through the system 400 times and the fortifying agent applied every 15 cycles or 6% of the time. The results are listed in Table II.

EXAMPLE 5

This experiment is a demonstration of a preferred embodiment of our fortification process, incorporating efficient organic removal, periodic fortification, and a provision for a holding time prior to the return of the acid to the alkylation reactor.

The initial acid charge is 1996g (1170cc) of 98% ashfree sulfuric acid. The acid was circulated for 400 cycles. After the 50th and 100 th cycle and then after every 100 cycles, the acid is diverted to an efficient separator, depressurized, cooled and fortified, under good agitation, with a quantity of synthetic converter gas, containing 10% $SO_3$, to return the water content to its original value of 2%. The return of the fortified acid to the alkylation reactor is delayed for 45 minutes.

The calculated build-up rates are: 0.5% $H_2O$ per 100 cycles; and 1.35% C per 100 cycles. As can be seen in Table II, above, these rates are somewhat smaller than those in the alkylation of Example 1 which operates without fortification. Therefore, fortification, in accordance with the present invention, does not effect undesirable side reactions, over and above those experienced in an alkylation process without fortification (Example 1).

EXAMPLE 6

This is a demonstration of an alternate preferred embodiment of the fortification process of the present invention, similar to Example 4.

The initial acid charge is 2200g (1200cc) of 98.8% $H_2SO_4$ with a 1.2% water content. The duration of the experiment is 450 cycles. The sulfuric acid is passed through an efficient separtor, depressurized and cooled before the application of the fortifying agent, 65% oleum. The fortifications, which return the water content of the acid to its initial value, are applied every 25 to 30 cycles or 3 to 4% of the time the acid is in contact with the hydrocarbons. The calculated build-up rates are 1.7% $H_2O$ per 100 cycles, and 2.0% C per 100 cycles. It is apparent that fortification, in accordance with our invention, works well even at about a 1% water content. Further, the type of fortifying agent does not matter, if applied in accordance with the present invention.

We claim:

1. In a process for alkylating hydrocrbons comprising an alkylation zone wherein alkylatable hydrocarbon feedstocks are contacted with alkylating agents in the presence of a concentrated sulfuric acid catalyst containing at least 1.0% but less than 4% water by weight, under alkylation conditions in an alkylation reactor, and wherein the alkylation phase is separated from the acid catalyst phase, the acid catalyst phase is cooled and recycled to the alkylation reactor, and wherein the water content of said acid catalyst phase is reduced by addition thereto of sulfur trioxide fortifying agents, the improvement which comprises:
   a. prior to the addition of said sulfur trioxide, removing hydrocarbons dispersed in said acid catalyst phase;
   b. periodically introducing said sulfur trioxide into said acid catalyst from step (a), said periodic introduction being for a time less than 6% of the time said acid catalyst is in contact with said hydrocarbons in said alkylation zone.
   c. cooling said fortified acid catalyst from step (b) to remove heat generated by said periodic introduction of said sulfur trioxide; and
   d. delaying the recycle of said cooled fortified acid catalyst from step (c) to the alkylation reactor for a time sufficient to allow substantially all of said sulfur trioxide to react with water present in said acid.

2. The process as described in claim 1 wherein said periodic introduction comprises less than 3% of the time said catalyst is in contact with said hydrocarbons in said alkylation zone.

3. The process as described in claim 1 wherein, prior to addition of said sulfur trioxide, the said acid catalyst is depressurized to remove volatile organic impurities dissolved in said acid catalyst.

4. The process as described in claim 1 wherein said cooled fortified acid catalyst is delayed for a period of time of at least 5 minutes and not more than 60 minutes.

5. The process as described in claim 1 wherein said cooled fortified acid catalyst is delayed for a period of time of at least 5 minutes and not more than 60 minutes at a temperature between 20° and 25° C.

* * * * *

UNITED STATES PATENT AND TRADEMARK OFFICE
CERTIFICATE OF CORRECTION

PATENT NO. : 4,148,836                  Page 1 of 2

DATED : April 10, 1979

INVENTOR(S) : R. L. Sturtevant, B. I. Karsay, and A. B. Gancy

It is certified that error appears in the above-identified patent and that said Letters Patent are hereby corrected as shown below:

Column 1, line 59, "specifications" should read -- specification --.

Column 2, line 29, "it" should read -- It --;

line 39, "subject" should read -- subjected --.

Column 3, line 38, "stble" should read -- stable --.

Column 4, line 24, "fortifiction" should read -- fortification --;

line 58, following "maintained" insert -- at --.

Column 5, line 19, following "55" insert -- into --;

line 24, following "13%" insert -- , --.

UNITED STATES PATENT AND TRADEMARK OFFICE
CERTIFICATE OF CORRECTION

PATENT NO. : 4,148,836

DATED : April 10, 1979

INVENTOR(S) : R. L. Sturtevant, B. I. Karsay, and A. B. Gancy

It is certified that error appears in the above-identified patent and that said Letters Patent are hereby corrected as shown below:

Column 5, line 66, following "30" insert -- minutes --.

Column 6, line 38, following "2.5%" insert -- , --;

line 63, "55.45" should read -- 55:45 --.

Column 7, line 28, following "4%" insert -- , --.

Column 8, line 44, following "2.8%" delete ".".

Column 9, line 36, "100 th" should read -- 100th --.

Column 10, line 2, "separtor" should read -- separator --;

line 15, "hydrocrbons" should read -- hydrocarbons --.

Signed and Sealed this

Eleventh Day of September 1979

[SEAL]

Attest:

Attesting Officer

LUTRELLE F. PARKER
Acting Commissioner of Patents and Trademarks